(12) United States Patent
Hirobe (10) Patent No.: US 11,045,611 B2
(45) Date of Patent: Jun. 29, 2021

(54) DRUG DELIVERING APPARATUS AND PRE-FILLED SYRINGE

(71) Applicant: NIPRO CORPORATION, Osaka (JP)

(72) Inventor: Teruhisa Hirobe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 386 days.

(21) Appl. No.: 15/573,695

(22) PCT Filed: Apr. 26, 2016

(86) PCT No.: PCT/JP2016/063059
§ 371 (c)(1),
(2) Date: Nov. 13, 2017

(87) PCT Pub. No.: WO2016/181826
PCT Pub. Date: Nov. 17, 2016

(65) Prior Publication Data
US 2018/0117264 A1 May 3, 2018

(30) Foreign Application Priority Data

May 14, 2015 (JP) .............................. JP2015-099185

(51) Int. Cl.
*A61M 5/34* (2006.01)
*A61M 5/28* (2006.01)
(Continued)

(52) U.S. Cl.
CPC .............. *A61M 5/34* (2013.01); *A61J 1/2096* (2013.01); *A61M 5/28* (2013.01); *A61M 5/3202* (2013.01);
(Continued)

(58) Field of Classification Search
CPC .............. A61M 2005/3104; A61J 1/201; A61J 1/2096; A61J 1/2013
See application file for complete search history.

(56) References Cited

U.S. PATENT DOCUMENTS 5,611,782 A    3/1997   Haedt
6,520,935 B1 * 2/2003   Jansen ................ A61M 5/3134
                                                                     604/111
(Continued)

FOREIGN PATENT DOCUMENTS

DE    102008013198 A1   9/2009
EP       0815884 A1    1/1998
(Continued)

OTHER PUBLICATIONS

Extended European Search Report, dated Nov. 14, 2018, for European Application No. 16792551.0.
(Continued)

*Primary Examiner* — Laura A Bouchelle
*Assistant Examiner* — Anh Bui
(74) *Attorney, Agent, or Firm* — Birch, Stewart, Kolasch & Birch LLP (57) ABSTRACT

A drug delivering apparatus includes a drug container, a pre-filled syringe including a cylindrical container having a nozzle portion and an injection needle attachment portion, and a connecting tool configured to allow communication between the inside of the cylindrical container and the inside of the drug container. The connecting tool further includes a nozzle insertion portion. The pre-filled syringe further includes a cap member configured to be detachably fitted on the injection needle attachment portion, the cap member having an opening into which the nozzle insertion portion can be inserted. The injection needle attachment portion has a guiding groove in the inner periphery thereof. In the state where the cap member is fitted on the injection attachment portion, at least a part of the edge of the opening is located on the inner side relative to the bottom portion of the guiding groove.

11 Claims, 8 Drawing Sheets

(51) Int. Cl.
  *A61J 1/20*  (2006.01)
  *A61M 5/32*  (2006.01)
  *A61M 5/20*  (2006.01)

(52) U.S. Cl.
  CPC ............ *A61M 5/3287* (2013.01); *A61J 1/201* (2015.05); *A61M 5/2033* (2013.01)

(56) References Cited

U.S. PATENT DOCUMENTS

| | | |
|---|---|---|
| 2004/0116858 A1 | 6/2004 | Heinz et al. |
| 2011/0015578 A1 | 1/2011 | Lowke |
| 2012/0123382 A1 | 5/2012 | Kubo |

FOREIGN PATENT DOCUMENTS

| | | | |
|---|---|---|---|
| EP | 1410819 A1 | 4/2004 | |
| JP | 2011-19704 A | 2/2011 | |
| JP | 2011-72440 A | 2/2011 | |
| JP | 2011-194045 A | 10/2011 | |
| JP | 2013-78443 A | 5/2013 | |
| JP | 2013078443 A * | 5/2013 | ............ A61M 5/347 |
| JP | 2014-79331 A | 5/2014 | |
| JP | 2014079331 A * | 5/2014 | |
| JP | 2014-200504 A | 10/2014 | |
| WO | WO 92/11897 A1 | 7/1992 | |
| WO | WO 2006/099441 A2 | 9/2006 | |

OTHER PUBLICATIONS

International Search Report, issued in PCT/JP2016/063059, PCT/ISA/210, dated Jun. 28, 2016.
Japanese Office Action, dated Jun. 2, 2020, for Japanese Application No. 2017-517869, with an English transliation.

* cited by examiner

DRUG DELIVERING APPARATUS AND PRE-FILLED SYRINGE

TECHNICAL FIELD

The present invention relates to a drug delivering apparatus to which an injection needle is to be attached so as to deliver a drug, and relates to a pre-filled syringe.

BACKGROUND ART

For preparing a drug to be delivered to a patient etc., a solution (liquid drug) (e.g., distilled water, a physiological saline solution, and a dextrose solution) in a medical container (e.g., a pre-filled syringe) has conventionally been injected into a drug container (e.g., a vial) with a dry drug contained therein, so that the dry drug is dissolved in the solution.

A connecting tool is used to connect the inside of a drug container and the inside of a pre-filled syringe. A drug prepared in the drug container is put into the pre-filled syringe through the connecting tool. An injection needle is attached by insertion to the pre-filled syringe filled with the drug, so that the drug can be delivered to a patient etc.

Examples of documents disclosing a connecting tool to allow communication between the inside of a pre-filled syringe and the inside of a drug container include Japanese Patent Laying-Open No. 2011-19704 (PTD 1) and Japanese Patent Laying-Open No. 2014-79331 (PTD 2).

Connecting tools disclosed in PTDs 1 and 2 each include a drug container insertion attachment portion provided on one end side and to which a mouth portion of a drug container is to be attached by insertion, a syringe insertion attachment portion provided on the other end side and to which the distal end of a pre-filled syringe (an injector) is to be attached by insertion, and a double-ended needle with which to pierce a sealing member sealing the mouth portion of the drug container and with which to pierce a lid member covering the opening at the distal end of the pre-filled syringe.

The pre-filled syringe is pushed toward the drug container in the state where the drug container is inserted in the drug container insertion attachment portion and where the pre-filled syringe is inserted in the syringe insertion attachment portion. As a result, the lid member is pierced with the other end needle of the double-ended needle. Subsequently, the pre-filled syringe and the connecting tool are pushed toward the drug container, so that the sealing member is pierced with the one end needle of the double-ended needle. Accordingly, the drug container is attached by insertion to the drug container insertion attachment portion, and the pre-filled syringe is attached by insertion to the syringe insertion attachment portion, so that the inside of the drug container and the inside of the pre-filled syringe communicate with each other.

The syringe insertion attachment portion is provided with a locking portion for locking onto the lid member of the pre-filled syringe. The locking portion locks the lid member when the pre-filled syringe is removed from the syringe insertion attachment portion. After a drug is prepared, the pre-filled syringe is removed from the connecting tool with the lid member off, thus allowing an injection needle to be attached to the distal end of the pre-filled syringe.

By permitting attachment of an injection needle after the pre-filled syringe and the drug container are connected to each other using the connecting tool, an injection needle can be prevented from being erroneously attached to the pre-filled syringe before the preparation.

A drug delivering apparatus has been developed that can prevent erroneous connection of an injection needle using a connecting tool different from the configurations in PTDs 1 and 2. Examples of documents that disclose such a drug delivering apparatus include Japanese Patent Laying-Open No. 2011-72440 (PTD 3).

A drug delivering apparatus disclosed in PTD 3 includes a pre-filled syringe, a connecting tool, and a drug container. The distal end of the pre-filled syringe is configured not to allow an injection needle to be attached thereto.

The connecting tool includes a connector member having an inner side into which the distal end of the pre-filled syringe can be inserted, and having an outer side to which an injection needle can be attached. The connecting tool also includes a puncture member having a connector member insertion attachment portion provided on one end side to detachably connect the connector member, and having a puncture needle provided on the other end side and with which a sealing member of the drug container can be pierced. The connecting tool also includes a guiding member having a cylindrical portion to which the puncture member is to be attached by insertion from one end side, the cylindrical portion providing a guide for movement of the puncture member toward the drug container. The guiding member also has a drug container insertion attachment portion provided on the other end side and to which a mouth portion of the drug container is to be attached by insertion.

The distal end of the pre-filled syringe is connected to the connector member that is attached by insertion to the connector member insertion attachment portion, and the pre-filled syringe is pushed toward the drug container. As a result, the puncture member moves in the guiding member. The movement of the puncture member allows the sealing member sealing the mouth portion of the drug container to be pierced with the puncture needle.

In the state where the puncture needle is through the sealing member, the puncture member is engaged with the guiding member and is thus prevented from being slipped from the guiding member. The connector member, on the other hand, is detachably fitted in the puncture member. Accordingly, after a drug is prepared, the pre-filled syringe is removed from the connecting tool in the state where the connector member is connected to the distal end of the pre-filled syringe.

By permitting attachment of an injection needle after the pre-filled syringe and the drug container are connected with each other, an injection needle can be prevented from being erroneously attached to the pre-filled syringe before the preparation.

CITATION LIST

Patent Document

PTD 1: Japanese Patent Laying-Open No. 2011-19704
PTD 2: Japanese Patent Laying-Open No. 2014-79331
PTD 3: Japanese Patent Laying-Open No. 2011-72440

SUMMARY OF INVENTION

Technical Problem

However, the connecting tools disclosed in PTDs 1 and 2 each include an inner cylindrical member and an outer cylindrical member, where the outer cylindrical member is configured to slide on the outer side of the inner cylindrical member when the lid member of the pre-filled syringe is pierced with one end needle of the double-ended needle. Further, the connecting tool is configured so that the inner cylindrical member is pushed into the drug container when the sealing member of the drug container is pierced with the other end needle of the double-ended needle. Therefore, the connecting tool disclosed in PTDs 1 and 2 involves structural complexity.

In the drug delivering apparatus disclosed in PTD 3, an injection needle needs to be attached to the connector member connected to the pre-filled syringe. This involves an increase in volume of a discharge path of a prepared drug compared to a case where an injection needle is directly attached to a nozzle portion of a pre-filled syringe. It is, therefore, concerned that a desired amount of drug cannot be delivered to a patient because of an increase in amount of residual liquid. Also, the inner periphery of the connector member needs to be processed into a shape that allows the distal end of the pre-filled syringe to be attached thereto, and the outer periphery of the connector member needs to be processed into a shape that allows an injection needle to be attached thereto. This leads to structural complication of the connector member.

The present invention has been made in view of the above problems. An object of the present invention is to provide a drug delivering apparatus and a pre-filled syringe that are simple in structure and that prevent an injection needle from being erroneously attached to a pre-filled syringe before a drug is prepared.

Solution to Problem

A drug delivering apparatus according to the present invention includes a drug container to contain a drug therein in a sealed manner; a pre-filled syringe including: a cylindrical container to contain a liquid drug therein, the cylindrical container including a nozzle portion provided on the distal end side, and a cylindrical injection needle attachment portion surrounding the nozzle portion and to which an injection needle is to be attached, and a plunger configured to be inserted into the cylindrical container from the proximal end side; and a connecting tool including a cylindrical body including: a receiving portion provided on one end side, the receiving portion being configured to be able to receive the nozzle portion and the injection needle attachment portion, and an insertion attachment portion provided on the other end side, the insertion attachment portion being configured to be attachable by insertion to the drug container, the connecting tool being configured to allow communication between the inside of the cylindrical container and the inside of the drug container in the state where the nozzle portion and the injection needle attachment portion are received in the receiving portion and where the drug container is attached by insertion to the insertion attachment portion. In the drug delivering apparatus according to the present invention, the connecting tool further includes: a partitioning portion partitioning the inside of the cylindrical body into a side where the receiving portion is disposed and a side where the insertion attachment portion is disposed, the partitioning portion having a through hole in the central portion thereof, and a cylindrical nozzle insertion portion provided on the side where the receiving portion is disposed so as to communicate with the through hole, the nozzle insertion portion being configured to be inserted between the nozzle portion and the injection needle attachment portion so that the nozzle portion is liquid-tightly inserted into the nozzle insertion portion. The pre-filled syringe further includes a cap member configured to be detachably fitted on the outer periphery of the injection needle attachment portion, the cap member having an opening. The injection needle attachment portion has a guiding groove in the inner periphery thereof, the guiding groove being configured to engage with an engagement protrusion provided at the proximal end of an injection needle, the guiding groove providing a guide for movement of an injection needle. The opening is configured to allow the nozzle insertion portion to be inserted therein, and is configured not to allow the proximal end portion of an injection needle to be inserted therein. In the state where the cap member is fitted on the outer periphery of the injection needle attachment portion, at least a part of the edge of the opening is located on the inner side relative to a bottom portion of the guiding groove when viewed in the axial direction of the nozzle portion.

In the drug delivering apparatus according to the present invention, the opening is preferably circular in shape, and the guiding groove preferably includes a spiral groove. In such a case, the inner diameter of the opening is preferably smaller than the root diameter of the spiral groove.

In the drug delivering apparatus according to the present invention, the cap member is preferably configured to be removed from the injection needle attachment portion when the pre-filled syringe is removed from the connecting tool.

In the drug delivering apparatus according to the present invention, the cylindrical body preferably includes a locking piece provided on the inner surface of the cylindrical body located on the side where the receiving portion is disposed. In such a case, the locking piece is preferably configured to lock the cap member when the pre-filled syringe is removed from the connecting tool.

In the drug delivering apparatus according to the present invention, the cap member is preferably shorter than the injection needle attachment portion in length along the axial direction of the nozzle portion. In such a case, the locking piece is preferably configured to lock a proximal end portion of the cap member.

A pre-filled syringe according to the present invention includes: a cylindrical container including a nozzle portion provided on a distal end portion, and a cylindrical injection needle attachment portion surrounding the nozzle portion and to which an injection needle is to be attached, and a plunger configured to be inserted into the cylindrical container from the proximal end side; and a cap member configured to be detachably fitted on the outer periphery of the injection needle attachment portion, the cap member having an opening. The injection needle attachment portion has a guiding groove in the inner periphery thereof, the guiding groove being configured to engage with an engagement protrusion provided at the proximal end of an injection needle, the guiding groove providing a guide for movement of an injection needle. The opening is configured to allow a stopper member to be inserted therein, the stopper member being configured to liquid-tightly seal the nozzle portion, the opening being configured not to allow the proximal end portion of an injection needle to be inserted therein. In the state where the cap member is fitted on the outer periphery of the injection needle attachment portion, at least a part of the edge of the opening is located on the inner side relative to a bottom portion of the guiding groove when viewed in the axial direction of the nozzle portion.

In the pre-filled syringe according to the present invention, the opening is preferably circular in shape, and the guiding groove preferably includes a spiral groove. In such a case the inner diameter of the opening is preferably smaller than the root diameter of the spiral groove.

Advantageous Effects of Invention

According to the present invention, a drug delivering apparatus and a pre-filled syringe can be provided that are simple in structure and that prevent an injection needle from being erroneously attached to a pre-filled syringe before a drug is prepared.

DESCRIPTION OF EMBODIMENTS

Embodiments of the present invention will be hereinafter described in detail with reference to the drawings. In the embodiments described below, the same or common components are designated by the same reference characters, and description thereof will not be repeated.

Figure 1:
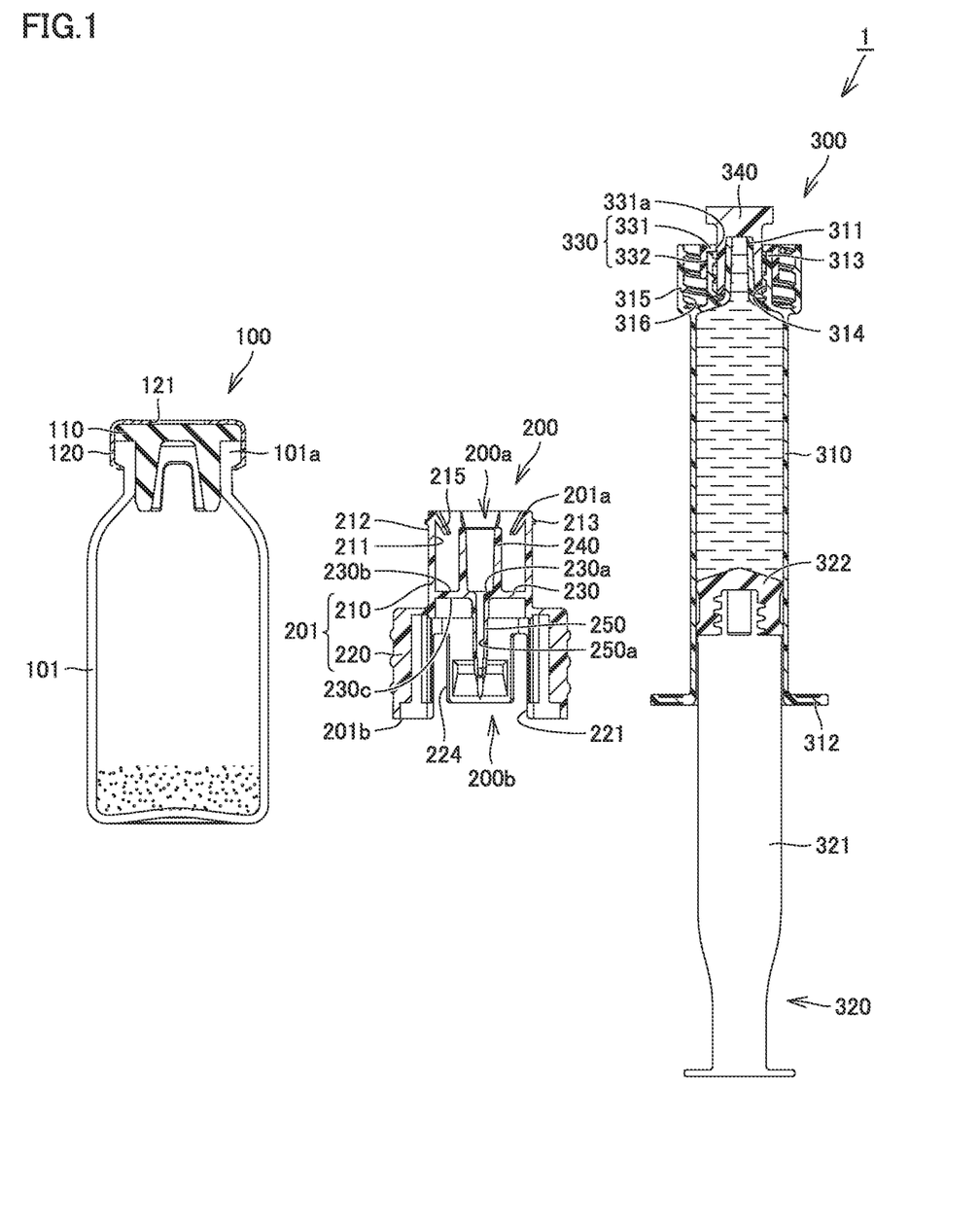
FIG. 1 is a cross-sectional view showing components of a drug delivering apparatus according to an embodiment of the present invention.

FIG. 1 is a cross-sectional view showing components of a drug delivering apparatus according to an embodiment of the present invention. A drug delivering apparatus according to the present embodiment will be described with reference to FIG. 1.

As shown in FIG. 1, a drug delivering apparatus 1 according to the present embodiment includes a drug container 100, a connecting tool 200, and a pre-filled syringe 300.

Drug container 100 is to contain a dry drug or a liquid drug as a drug therein. Drug container 100 includes a container body 101 having a mouth portion 101a and includes a closing member 110 to close mouth portion 101a. Closing member 110 is fixed to the head of drug container 100 with a ring member 120. Closing member 110 may be made of a rubber member and a thermoplastic elastomer resin.

The central portion of closing member 110 is formed to be thin-walled. The central portion of closing member 110 can be punctured with a puncture needle 250 of connecting tool 200, which is described later.

Ring member 120 surrounds the head portion of container body 101 and closing member 110 from the outer periphery side so as to integrally fasten them. Ring member 120 has an opening 121 through which the central portion of closing member 110 is exposed.

Connecting tool 200 is to allow communication between the inside of drug container 100 and the inside of pre-filled syringe 300. Connecting tool 200 includes a cylindrical body 201, a partitioning portion 230, a nozzle insertion portion 240, and puncture needle 250.

Cylindrical body 201 includes a receiving portion 200a on the one end 201a side, the receiving portion 200a being configured to receive a nozzle portion 311 and an injection needle attachment portion 313 of pre-filled syringe 300 described later. Cylindrical body 201 also includes an insertion attachment portion 200b on the other end 201b side, the insertion attachment portion 200b being configured to be attachable to drug container 100.

Cylindrical body 201 is constituted of a first cylindrical portion 210 and a second cylindrical portion 220. First cylindrical portion 210 and second cylindrical portion 220 have a common central axis. First cylindrical portion 210 and second cylindrical portion 220 are integrally formed by, for example, injection molding.

First cylindrical portion 210 is provided with a protruding portion 213 and locking pieces 215 on one end side. Protruding portion 213 is provided on outer periphery 212 of first cylindrical portion 210. Protruding portion 213 protrudes from the outer periphery of first cylindrical portion 210 to the radially outer side. Protruding portion 213 is to engage with a spiral groove 316 of a connecting tool attachment portion 315 provided at pre-filled syringe 300 described later.

Locking pieces 215 are provided on inner periphery 211 of first cylindrical portion 210. Locking pieces 215 are directed to the radially inner side of cylindrical body 201 as coming closer to partitioning portion 230. There are a plurality of locking pieces 215 circumferentially at a pitch of, for example, 90°. The number and positions of locking pieces 215 may be changed as appropriate.

Locking pieces 215 are parts for locking a later-described cap member 330 so that cap member 330 is removed when pre-filled syringe 300 is removed from connecting tool 200.

Second cylindrical portion 220 is provided to be attachable by insertion to mouth portion 101a of drug container 100. The inner diameter of second cylindrical portion 220 is slightly smaller than mouth portion 101a. In the state where second cylindrical portion 220 is inserted in mouth portion 101a, second cylindrical portion 220 is expanded outward and inner periphery 221 of second cylindrical portion 220 catches the outer periphery of mouth portion 101a.

Second cylindrical portion 220 has a cutout portion 224. Cutout portion 224 facilitates deflection and deformation of second cylindrical portion 220, thus facilitating attachment by insertion of second cylindrical portion 220 to mouth portion 101a.

Inner periphery 221 of second cylindrical portion 220 is provided to be slidable on the outer periphery of mouth portion 101a. In the state where second cylindrical portion 220 is inserted in mouth portion 101a, cylindrical body 201 can be pushed toward drug container 100.

Partitioning portion 230 partitions the inside of cylindrical body 201 into the side where receiving portion 200a is disposed and the side where insertion attachment portion 200b is disposed. Partitioning portion 230 has a disk shape. Partitioning portion 230 has a through hole 230a in the central portion thereof.

Nozzle insertion portion 240 is provided on a main surface 230b of partitioning portion 230 located on the one end 201a side. Nozzle insertion portion 240 extends from main surface 230b toward one end 201a of cylindrical body 201. Nozzle insertion portion 240 is cylindrical in shape.

The inside of nozzle insertion portion 240 communicates with through hole 230a. In nozzle insertion portion 240, nozzle portion 311 of pre-filled syringe 300 is to be liquid-tightly inserted.

Puncture needle 250 is provided on a main surface 230c of partitioning portion 230 located on the other end 201b side. Puncture needle 250 extends from main surface 230c toward the other end 201b of cylindrical body 201. Puncture needle 250 has a hollow passage 250a communicating with through hole 230a. Puncture needle 250 is provided to be able to pierce closing member 110 described above.

First cylindrical portion 210, partitioning portion 230, and nozzle insertion portion 240 described above constitute receiving portion 200a for receiving nozzle portion 311 and injection needle attachment portion 313. Nozzle portion 311 is to be inserted into nozzle insertion portion 240, and injection needle attachment portion 313 is to be inserted into the gap between nozzle insertion portion 240 and first cylindrical portion 210.

When nozzle portion 311 is fitted in nozzle insertion portion 240, and nozzle portion 311 and injection needle attachment portion 313 cannot easily move toward partitioning portion 230, nozzle portion 311 and injection needle attachment portion 313 are in the state of being received in receiving portion 200a.

Second cylindrical portion 220 described above constitutes insertion attachment portion 200b attachable to drug container 100. When second cylindrical portion 220 is fitted on drug container 100 and cannot easily move toward drug container 100, drug container 100 is in the state of being attached by insertion to insertion attachment portion 200b.

Pre-filled syringe 300 includes a cylindrical container 310, a plunger 320, cap member 330, and a stopper member 340.

Cylindrical container 310 includes nozzle portion 311 provided on the distal end side, a flange portion 312 provided on the proximal end side, injection needle attachment portion 313 provided on the outer side of nozzle portion 311, and connecting tool attachment portion 315 provided on the outer side of injection needle attachment portion 313.

Nozzle portion 311 is provided to be able to discharge a liquid drug contained in cylindrical container 310. As the liquid drug, solutions (e.g., a physiological saline solution and a dextrose solution) or drug solutions may be used.

Flange portion 312 protrudes from the proximal end of cylindrical container 310 to the radially outer side thereof. Flange portion 312 can be held with the tips of fingers, such as an index finger and a middle finger.

Injection needle attachment portion 313 is provided so as to surround nozzle portion 311. Injection needle attachment portion 313 is a part to which an injection needle 400 (see FIG. 8), which is described later, is to be attached. Injection needle attachment portion 313 is substantially cylindrical in shape. Injection needle attachment portion 313 has a spiral groove 314 as a guiding groove in the inner periphery thereof.

Spiral groove 314 is to engage with an engagement protrusion 421 (see FIG. 8) provided at the proximal end of injection needle 400. That is, root diameter L2 (see FIG. 2) of spiral groove 314, which is described later, is slightly larger than the outer diameter of engagement protrusion 421. Note that root diameter L2 of spiral groove 314 refers to the distance between the bottom portions of spiral groove 314. Spiral groove 314 provides a guide for movement of injection needle 400 when injection needle 400 is attached to injection needle attachment portion 313.

Connecting tool attachment portion 315 is provided so as to surround injection needle attachment portion 313. Connecting tool attachment portion 315 is a part to which one end side of connecting tool 200 is to be attached. Connecting tool attachment portion 315 is substantially cylindrical in shape. Connecting tool attachment portion 315 has a spiral groove 316 in the inner periphery thereof.

Spiral groove 316 is to engage with protruding portion 213 provided at one end portion of connecting tool 200. Spiral groove 316 provides a guide for movement of connecting tool 200 when connecting tool 200 is attached to connecting tool attachment portion 315.

Plunger 320 is to be inserted into cylindrical container 310 from the proximal end side of cylindrical container 310. Plunger 320 includes a plunger rod 321 and a gasket 322 attached to the distal end of plunger rod 321. Gasket 322 is provided to be slidable on the inner periphery of cylindrical container 310. Gasket 322 allows the inside of cylindrical container 310 to be kept in a liquid-tight state.

Cap member 330 is to be detachably fitted on the outer periphery of injection needle attachment portion 313. Cap member 330 includes a top board portion 331 and a peripheral wall portion 332. Top board portion 331 has a disk shape. Top board portion 331 has a circular opening 331a substantially in the central portion thereof. When viewed in the axial direction of nozzle portion 311, opening 331a allows nozzle portion 311 to be exposed therethrough. Peripheral wall portion 332 is cylindrical in shape and is provided so as to be continuous with the periphery of top board portion 331.

Opening 331a is configured not to allow the proximal end portion of injection needle 400 to be inserted therein. Specifically, bore L1 (see FIG. 2) of opening 331a is smaller than the outer diameter of engagement protrusion 421 of injection needle 400. Further, bore L1 of opening 331a is smaller than root diameter L2 of spiral groove 314.

Figure 2:
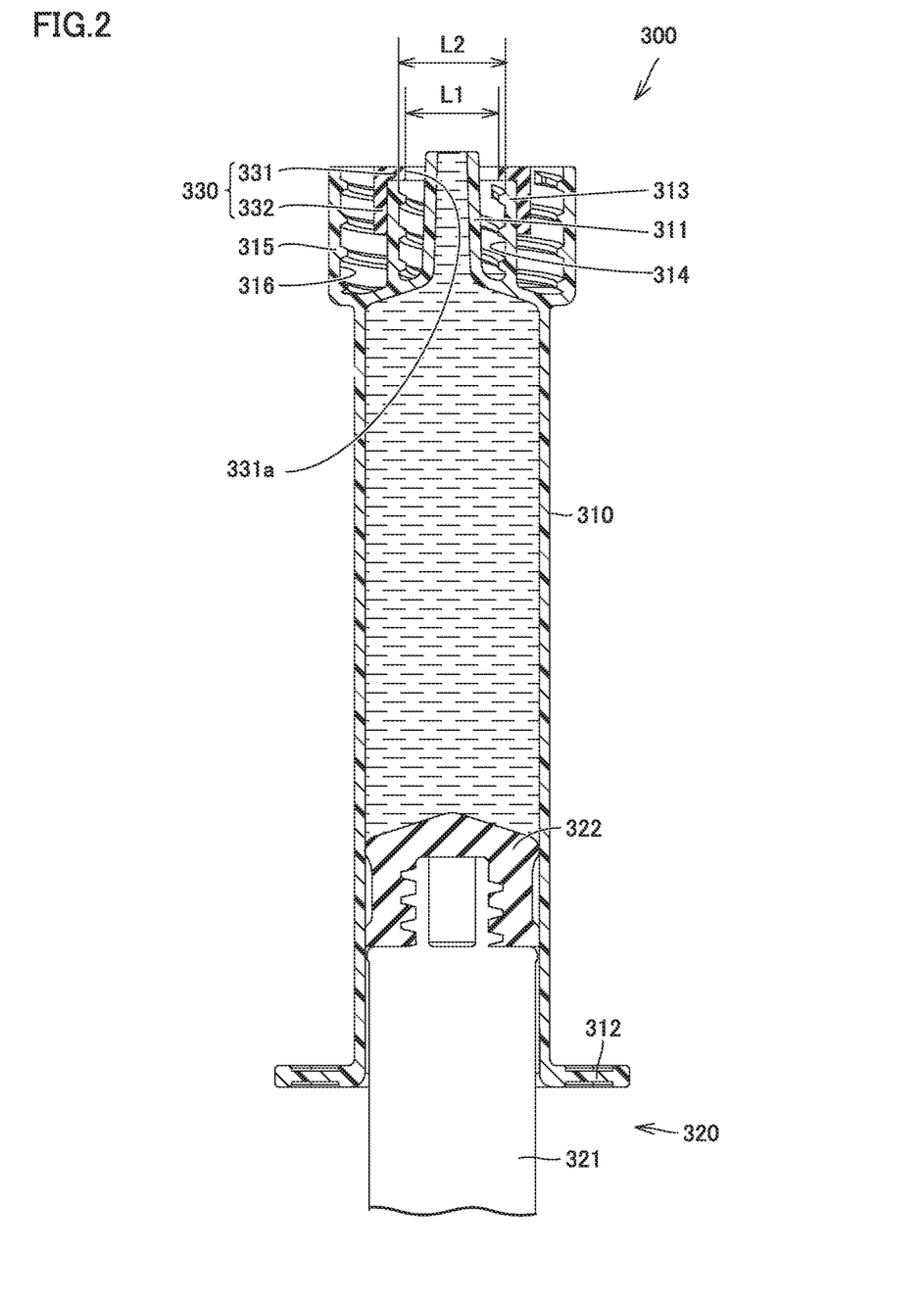
FIG. 2 is a cross-sectional view showing a first step when the drug delivering apparatus shown in FIG. 1 is used, FIG. 2 being an enlarged view of the distal end side of a pre-filled syringe.

By setting bore L1 of opening 331a to be smaller than the outer diameter of engagement protrusion 421 and by setting bore L1 of opening 331a to be smaller than root diameter L2 of spiral groove 314, cap member 330 makes it impossible for injection needle 400 to be attached to injection needle attachment portion 313 in the state where cap member 330 is fitted on injection needle attachment portion 313. Note that, by setting bore L1 of opening 331a to be smaller than the inner diameter (the distance between crest portions) of spiral groove 314, attachment of injection needle 400 to injection needle attachment portion 313 can be made impossible more reliably.

Stopper member 340 is to be detachably attached to nozzle portion 311. Stopper member 340 is in the form of a bottomed cylinder. Stopper member 340 liquid-tightly seals nozzle portion 311 while being attached to nozzle portion 311.

One end side of stopper member 340, which is located opposite to the bottom that faces the distal end of nozzle portion 311, is provided to be able to be inserted into opening 331a of cap member 330. Also, the one end side of stopper member 340 is to be inserted into the gap between the outer periphery of nozzle portion 311 and the inner periphery of injection needle attachment portion 313.

Specifically, the outer diameter of the one end side of stopper member 340 is smaller than the bore of opening 331a. Further, the outer diameter of the one end side of stopper member 340 is smaller than the inner diameter of spiral groove 314.

FIG. 2 is a cross-sectional view showing a first step when the drug delivering apparatus shown in FIG. 1 is used, FIG.

2 being an enlarged view of the distal end side of the pre-filled syringe. FIGS. 3 to 8 are cross-sectional views showing second to seventh steps when the drug delivering apparatus shown in FIG. 1 is used. With reference to FIGS. 2 to 8, the operation of drug delivering apparatus 1 in use according to the present embodiment will be described.

In using drug delivering apparatus 1, drug container 100 with a drug contained therein in a sealed manner, connecting tool 200, and pre-filled syringe 300 with a liquid drug contained therein are separately prepared first. As to pre-filled syringe 300, the one whose cap member 330 is fitted on the outer periphery of injection needle attachment portion 313 and whose nozzle portion 311 is sealed by stopper member 340 is prepared.

Then, as shown in FIG. 2, in the first step, stopper member 340 is detached from pre-filled syringe 300. At this time, it is preferable that stopper member 340 be detached in the state where nozzle portion 311 is directed upward so that the liquid drug will not be leaked out of nozzle portion 311.

Figure 3:
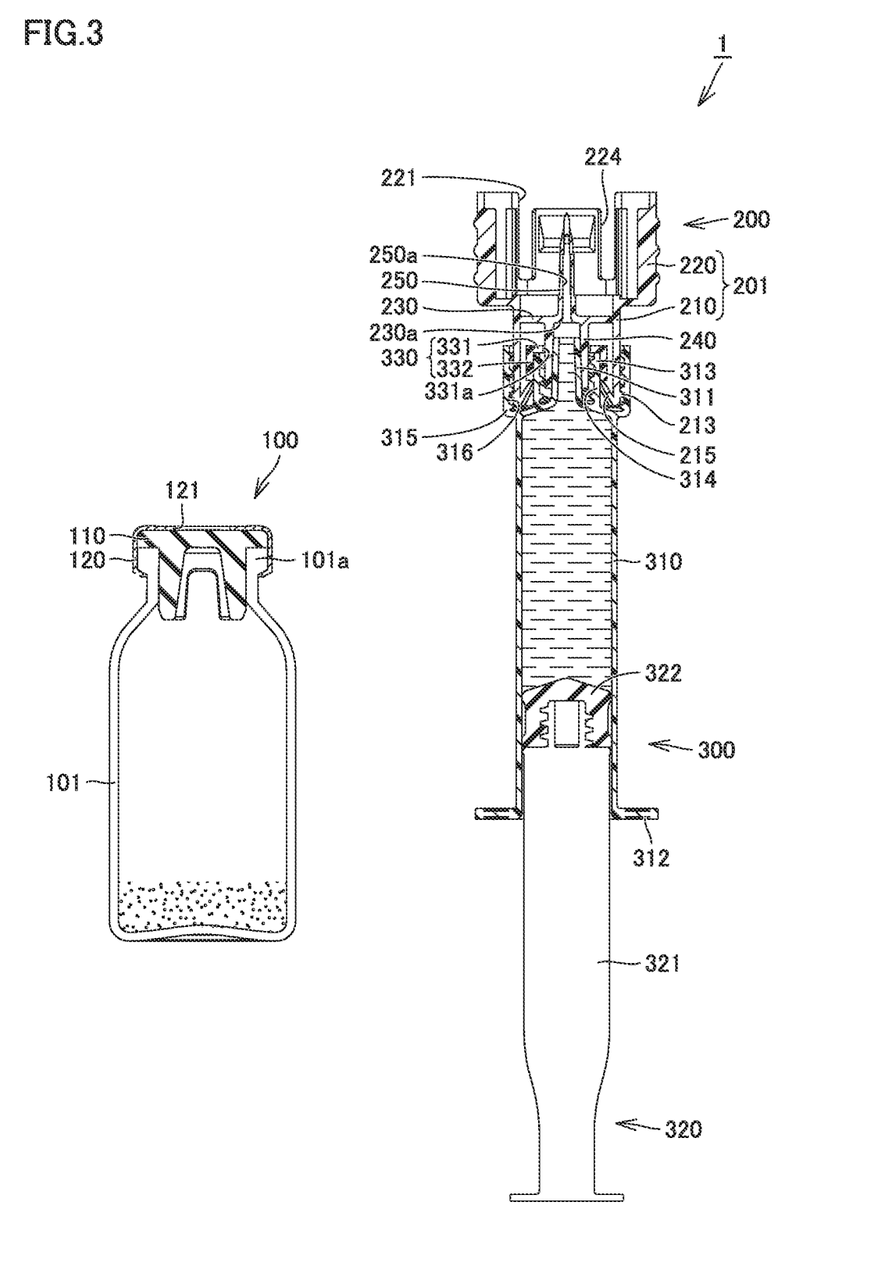
FIG. 3 is a cross-sectional view showing a second step when the drug delivering apparatus shown in FIG. 1 is used.

Subsequently, as shown in FIG. 3, in the second step, connecting tool 200 is attached to the distal end of pre-filled syringe 300 in the state where nozzle portion 311 is directed upward. Specifically, connecting tool 200 is rotated around the axis of cylindrical body 201 while protruding portion 213 on the outer periphery of first cylindrical portion 210 is engaged with spiral groove 316 of connecting tool attachment portion 315.

By moving protruding portion 213 along and relative to spiral groove 316, nozzle insertion portion 240 passes through opening 331a of cap member 330 and is inserted into the gap between nozzle portion 311 and injection needle attachment portion 313.

By moving connecting tool 200 ahead by a predetermined distance toward pre-filled syringe 300 along the axial direction of cylindrical body 201 while moving protruding portion 213 ahead along and relative to spiral groove 316, nozzle portion 311 is liquid-tightly attached by insertion to nozzle insertion portion 240.

The distance between distal end portions of locking pieces 215 that face each other is smaller than the outer diameter of peripheral wall portion 332 of cap member 330. Accordingly, when connecting tool 200 moves ahead toward pre-filled syringe 300 along the axial direction of cylindrical body 201, locking pieces 215 are forced open by cap member 330. After the entire cap member 330 has passed through and relative to locking pieces 215, locking pieces 215 restore to the original shape. In this way, locking pieces 215 can lock the proximal end side of cap member 330.

Figure 4:
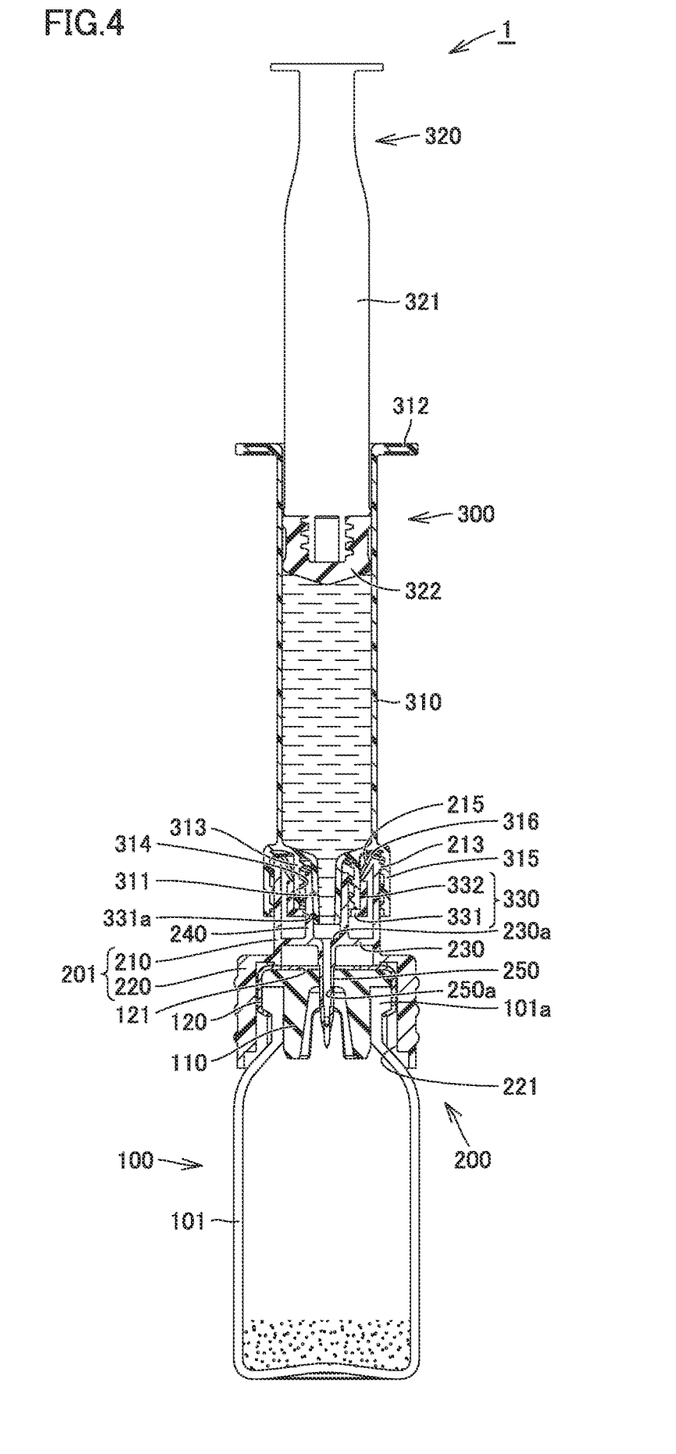
FIG. 4 is a cross-sectional view showing a third step when the drug delivering apparatus shown in FIG. 1 is used.

Subsequently, as shown in FIG. 4, in the third step, second cylindrical portion 220 of connecting tool 200 is fitted on mouth portion 101a of drug container 100, and connecting tool 200 is pushed toward drug container 100. This allows closing member 110 of drug container 100 to be pierced with puncture needle 250. As a result, the inside of pre-filled syringe 300 and the inside of drug container 100 communicate with each other through hollow passage 250a of puncture needle 250. Connecting tool 200 thus allows communication between the inside of cylindrical container 310 and the inside of drug container 100 in the state where nozzle portion 311 and injection needle attachment portion 313 are received in receiving portion 200a and where drug container 100 is attached by insertion to insertion attachment portion 200b.

Note that, in order to stably push connecting tool 200 in, it is preferable that connecting tool 200 be pushed down in the state where nozzle portion 311 of pre-filled syringe 300 is directed downward and where drug container 100 is located below second cylindrical portion 220.

Figure 5:
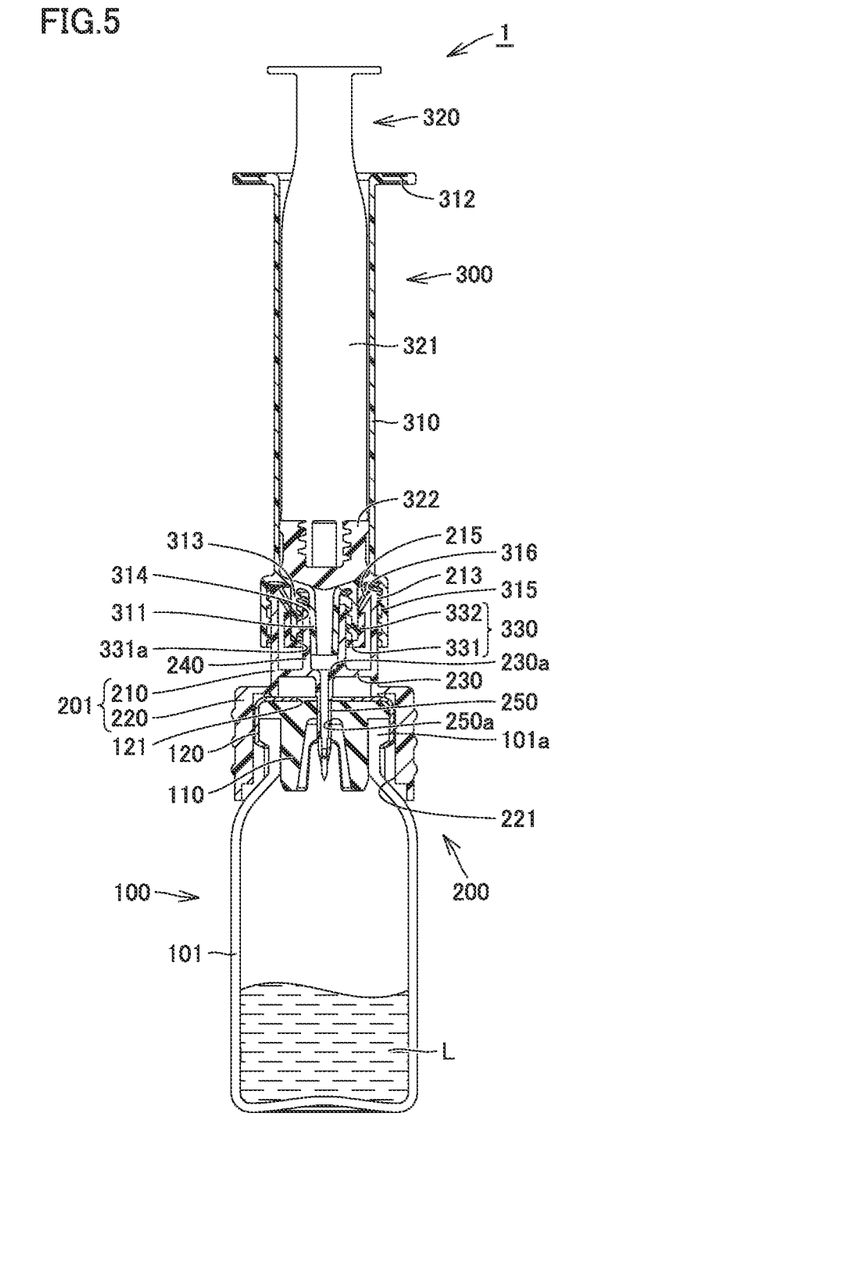
FIG. 5 is a cross-sectional view showing a fourth step when the drug delivering apparatus shown in FIG. 1 is used.

Next, as shown in FIG. 5, in the fourth step, plunger 320 is pushed toward drug container 100, and the liquid drug contained in pre-filled syringe 300 is transferred into drug container 100 through nozzle portion 311, through hole 230a, and hollow passage 250a of puncture needle 250. The drug and the liquid drug are mixed in drug container 100 so that a drug L is prepared.

Figure 6:
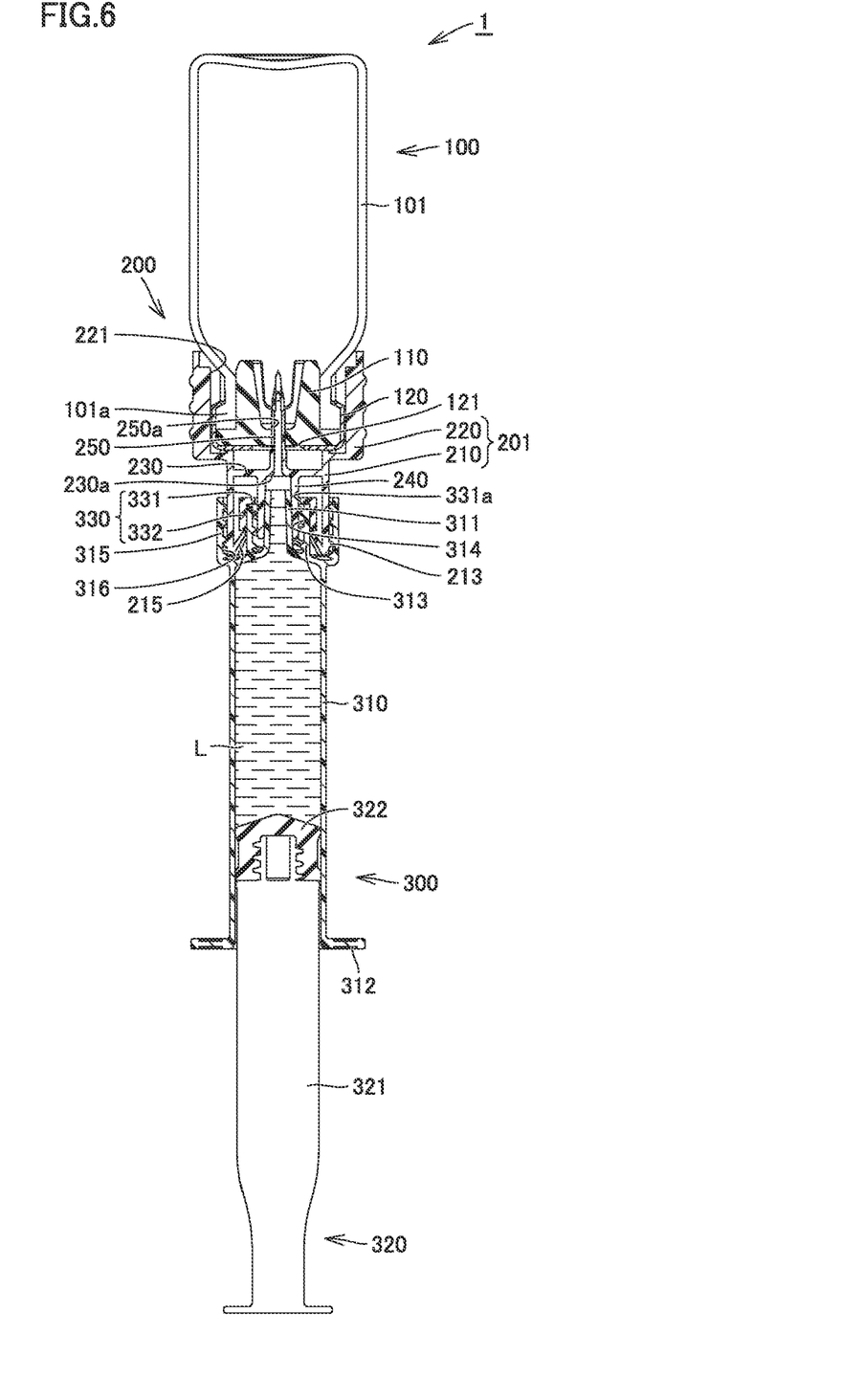
FIG. 6 is a cross-sectional view showing a fifth step when the drug delivering apparatus shown in FIG. 1 is used.

Subsequently, as shown in FIG. 6, in the fifth step, plunger 320 is retracted toward the proximal end side of cylindrical container 310 in the state where drug container 100 and pre-filled syringe 300 are connected with each other with connecting tool 200 and where nozzle portion 311 is directed upward. The retraction of plunger 320 causes drug L prepared in drug container 100 to be drawn into pre-filled syringe 300.

Figure 7:
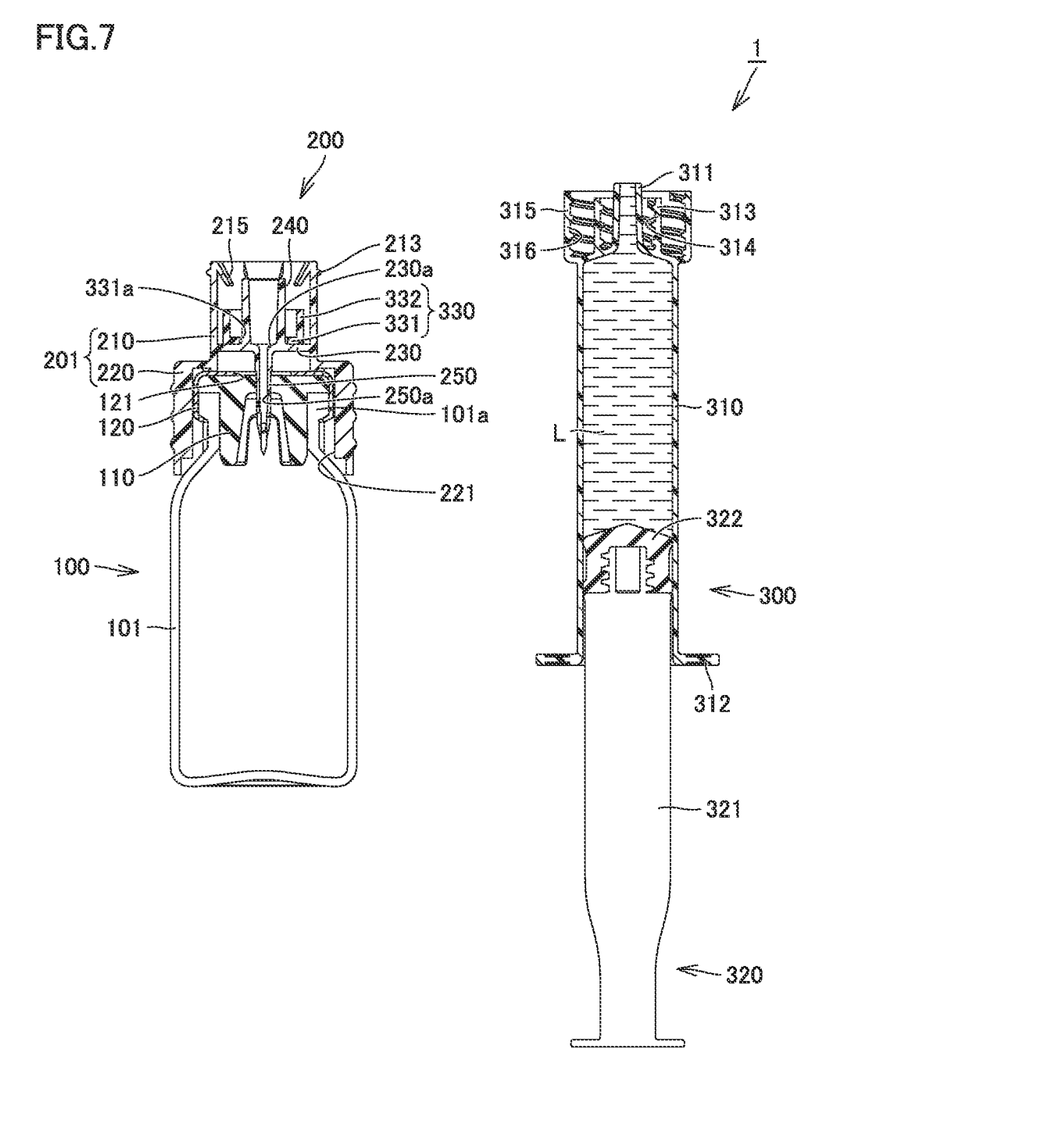
FIG. 7 is a cross-sectional view showing a sixth step when the drug delivering apparatus shown in FIG. 1 is used.

Next, as shown in FIG. 7, in the sixth step, pre-filled syringe 300 is removed from connecting tool 200. Specifically, connecting tool 200 is rotated around the axis of cylindrical body 201 in the state where nozzle portion 311 is directed upward. At this time, connecting tool 200 is rotated in the direction opposite to the rotation direction in the second step.

By retracting protruding portion 213 along and relative to spiral groove 316, connecting tool 200 moves away from pre-filled syringe 300. At this time, nozzle insertion portion 240 gets away from nozzle portion 311 through opening 331a of cap member 330. Nozzle portion 311 is thus pulled away from nozzle insertion portion 240.

When connecting tool 200 moves away from pre-filled syringe 300, locking pieces 215 lock a proximal end portion of cap member 330. Accordingly, when connecting tool 200 moves, injection needle attachment portion 313 retracts relative to cap member 330. The retraction of injection needle attachment portion 313 by a predetermined distance relative to cap member 330 causes cap member 330 to be removed from injection needle attachment portion 313. The removed cap member 330 is put into the gap between nozzle insertion portion 240 and first cylindrical portion 210.

In this way, with cap member 330 off from injection needle attachment portion 313, pre-filled syringe 300 is removed from connecting tool 200. The removal of cap member 330 allows injection needle 400 to be attached to injection needle attachment portion 313.

Figure 8:
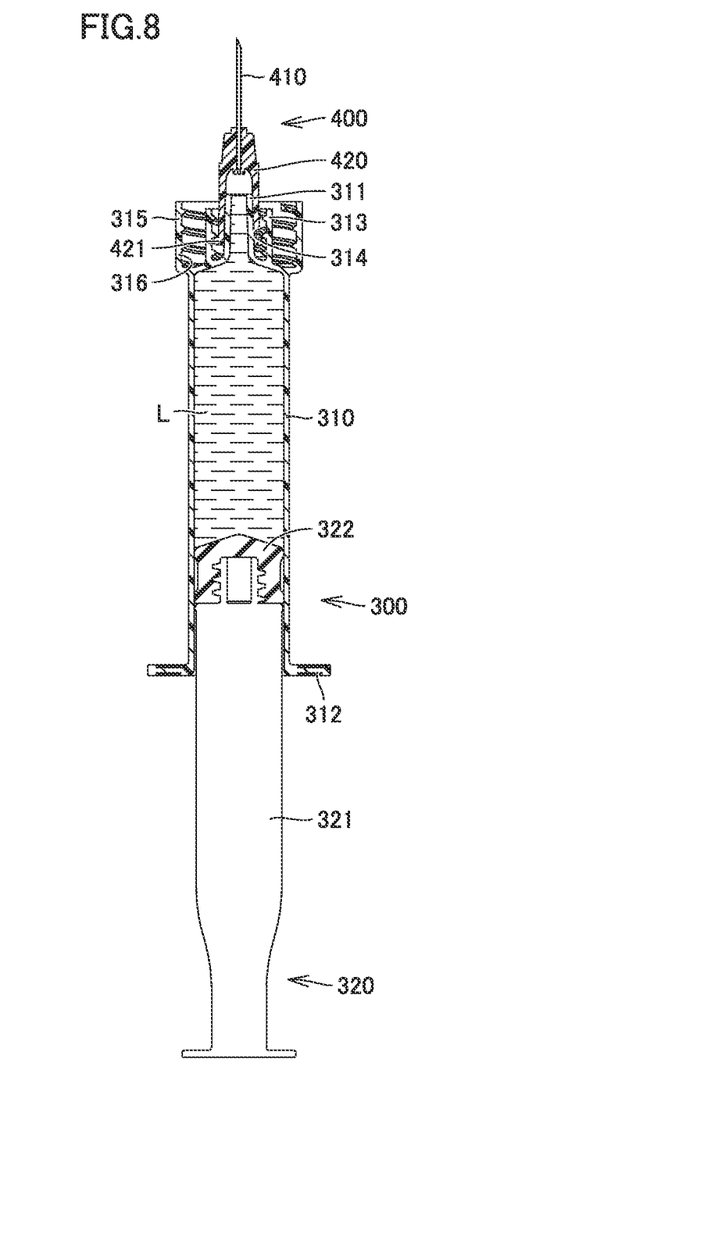
FIG. 8 is a cross-sectional view showing a seventh step when the drug delivering apparatus shown in FIG. 1 is used.

Subsequently, as shown in FIG. 8, in the seventh step, injection needle 400 is attached to injection needle attachment portion 313. Injection needle 400 includes a needle tube 410 and a needle hub 420. Needle hub 420 has engagement protrusion 421 at the proximal end thereof, engagement protrusion 421 protruding to the radially outer side. Engagement protrusion 421 is provided to be able to engage with spiral groove 314 of injection needle attachment portion 313.

Injection needle 400 can be attached to injection needle attachment portion 313 by rotating injection needle 400 around its axis while engagement protrusion 421 is engaged with spiral groove 314.

As described above, in drug delivering apparatus 1 according to the present embodiment, attachment of cap member 330 to injection needle attachment portion 313 of pre-filled syringe 300 makes it impossible for injection needle 400 to be attached to injection needle attachment portion 313. Cap member 330 is constituted of top board portion 331 having opening 331a in the central portion thereof, and cylindrical peripheral wall portion 332 continuous with the periphery of top board portion 331. This allows cap member 330 to be simple in structure, thus allowing drug delivering apparatus 1 to be simple in structure.

Further, in drug delivering apparatus 1, cap member 330 remains attached to injection needle attachment portion 313 until preparation of drug L is completed by mixing a drug in drug container 100 and a liquid drug in pre-filled syringe 300 while the inside of drug container 100 and the inside of pre-filled syringe 300 are connected with each other with connecting tool 200.

Removal of cap member 330 from injection needle attachment portion 313 is permitted after the completion of preparation of drug L. Therefore, a user can avoid erroneously attaching injection needle 400 to injection needle attachment portion 313 before a drug is prepared.

Further, a user has to successively carry out the operations in the first to sixth steps described above before cap member 330 is removed, and thus will attach an injection needle with an awareness of the procedures. In this respect, too, a user can avoid erroneously attaching injection needle 400 to injection needle attachment portion 313 before drug L is prepared.

Further, when pre-filled syringe 300 is removed from connecting tool 200 while cap member 330 is locked by locking pieces 215, cap member 330 is removed from injection needle attachment portion 313. This eliminates the need for a user to directly remove cap member 330, thus saving a user's trouble.

Connecting tool 200 includes cylindrical body 201 constituted of first cylindrical portion 210 and second cylindrical portion 220, cylindrical body 201 being divided by partitioning portion 230 into two sections in the axial direction. Further, connecting tool 200 is provided with cylindrical nozzle insertion portion 240 on the first cylindrical portion 210 side, and is provided with a puncture needle on the second cylindrical portion 220 side.

With connecting tool 200 being configured as above, closing member 110 of drug container 100 can be pierced with the puncture needle by pushing cylindrical body 201 toward drug container 100 after pre-filled syringe 300 is inserted into the first cylindrical portion 210 side and after drug container 100 is inserted into the second cylindrical portion 220 side. Therefore, there is no need to provide a sliding mechanism for relative movement of first cylindrical portion 210 and second cylindrical portion 220 with respect to each other. This allows connecting tool 200 to be simple in structure, thus allowing drug delivering apparatus 1 to be simple in structure.

As described above, drug delivering apparatus 1 and pre-filled syringe 300 according to the present embodiment are simple in structure. Using these, injection needle 400 can be prevented from being erroneously attached to pre-filled syringe 300 before a drug is prepared.

The above embodiment illustrates the case where locking pieces 215 are provided in cylindrical body 201. The embodiment, however, is not limited to this. Locking pieces 215 do not necessarily have to be provided.

In such a case, cap member 330 remains fitted on injection needle attachment portion 313 when pre-filled syringe 300 is removed from connecting tool 200 after preparation of a drug. Accordingly, a user removes cap member 330 from injection needle attachment portion 313 and then attaches injection needle 400 to injection needle attachment portion 313.

The above embodiment illustrates the case where opening 331a of cap member 330 is circular in shape. The embodiment, however, is not limited to this. Opening 331a may be, for example, polygonal and elliptical in shape as long as opening 331a is configured to allow nozzle insertion portion 240 to be inserted therein and not to allow the proximal end side of injection needle 400 to be inserted therein.

Further, the above embodiment illustrates the case where, in the state where cap member 330 is fitted on the outer periphery of injection needle attachment portion 313, the whole edge of opening 331a of cap member 330 is located on the inner side relative to the root diameter of spiral groove 314 provided in the inner periphery of injection needle attachment portion 313 when viewed in the axial direction of nozzle portion 311. The embodiment, however, is not limited to this. Other configuration may be possible as long as opening 331a is configured to allow nozzle insertion portion 240 to be inserted therein and not to allow the proximal end side of injection needle 400 to be inserted therein, and as long as at least a part of the edge of opening 331a is located on the inner side relative to the root diameter of spiral groove 314. For example, cap member 330 may include a protruding portion protruding from at least a part of the edge of opening 331a to the radially inner side.

Further, the above embodiment illustrates the case where the guiding groove provided in the inner periphery of injection needle attachment portion 313 is spiral groove 314. The embodiment, however, is not limited to this but may be modified as appropriate to any configuration that allows attachment of an injection needle.

Although embodiments of the present invention have been described as above, the embodiments disclosed herein are illustrative and non-restrictive in every respect. The scope of the present invention is defined by the terms of the claims, and includes any modification within the meaning and scope equivalent to the terms of the claims.

REFERENCE SIGNS LIST

1: drug delivering apparatus;
100: drug container;
101: container body;
101a: mouth portion;
110: closing member;
120: ring member;
121: opening;
200: connecting tool;
200a: receiving portion;
200b: insertion attachment portion;
201: cylindrical body;
201a: one end;
201b: the other end;
210: first cylindrical portion;
213: protruding portion;
215: locking piece;
220: second cylindrical portion;
221: inner periphery;
224: cutout portion;
230: partitioning portion;
230a: through hole;
230b, 230c: main surface;
231: protruding portion;
240: nozzle insertion portion;
250: puncture needle;
250a: hollow passage;
300: pre-filled syringe;
310: cylindrical container;
311: nozzle portion;
312: flange portion;
313: injection needle attachment portion;
314: spiral groove;

315: connecting tool attachment portion;
316: spiral groove;
320: plunger;
321: plunger rod;
322: gasket;
330: cap member;
331: top board portion;
331a: opening;
332: peripheral wall portion;
340: stopper member;
400: injection needle;
410: needle tube;
420: needle hub;
421: engagement protrusion.

The invention claimed is:

1. A drug delivering apparatus comprising:
a drug container to contain a drug therein in a sealed manner;
a pre-filled syringe including:
a cylindrical container to contain a liquid drug therein, the cylindrical container including a nozzle portion provided on a distal end side, and a cylindrical injection needle attachment portion radially spaced from and surrounding the nozzle portion to form a first space and to which an injection needle is to be attached and a connecting tool attachment portion radially spaced from and surrounding the injection needle attachment portion to form a second space;
a cap member configured to be detachably fitted on an outer periphery of the injection needle attachment portion, the cap member having a sidewall extending into the second space and a top wall having an opening in a center of the top wall; and
a plunger configured to be inserted into the cylindrical container from a proximal end side of the cylindrical container; and
a connecting tool including a cylindrical body including:
a receiving portion provided on one end side, the receiving portion being configured to be able to receive the nozzle portion and the injection needle attachment portion,
an insertion attachment portion provided on the other end side, the insertion attachment portion being configured to be attachable by insertion to the drug container,
the connecting tool being configured to allow communication between inside of the cylindrical container and inside of the drug container in a state where the nozzle portion and the injection needle attachment portion are received in the receiving portion and where the drug container is attached by insertion to the insertion attachment portion,
the connecting tool further including:
a partitioning portion partitioning inside of the cylindrical body into a side where the receiving portion is disposed and a side where the insertion attachment portion is disposed, the partitioning portion having a through hole in a central portion thereof, and
a cylindrical nozzle insertion portion provided on the side where the receiving portion is disposed so as to communicate with the through hole, the nozzle insertion portion being configured to be inserted into the first space between the nozzle portion and the injection needle attachment portion so that the nozzle portion is liquid-tightly inserted into the nozzle insertion portion, wherein the injection needle attachment portion has a guiding groove in an inner periphery thereof, the guiding groove being configured to engage with an engagement protrusion provided at a proximal end of an injection needle, the guiding groove providing a guide for movement of an injection needle,
wherein the opening of the cap member is larger than a diameter of the nozzle portion and smaller than an inner diameter of the injection needle attachment portion to allow the nozzle insertion portion to be inserted therein, and configured not to allow the proximal end portion of an injection needle to be inserted therein, and
wherein, in a state where the cap member is fitted into the second space and on the outer periphery of the injection needle attachment portion, at least a part of an edge of the opening is located on an inner side relative to a bottom portion of the guiding groove when viewed in an axial direction of the nozzle portion.

2. The drug delivering apparatus according to claim 1, wherein the opening is circular in shape,
wherein the guiding groove comprises a spiral groove, and
wherein an inner diameter of the opening is smaller than a root diameter of the spiral groove.

3. The drug delivering apparatus according to claim 1, wherein the cap member is configured to be removed from the injection needle attachment portion when the pre-filled syringe is removed from the connecting tool.

4. The drug delivering apparatus according to claim 3, wherein the cylindrical body includes a locking piece provided on an inner surface of the cylindrical body located on the side where the receiving portion is disposed, and
wherein the locking piece is configured to lock the cap member when the pre-filled syringe is removed from the connecting tool.

5. The drug delivering apparatus according to claim 4, wherein the cap member is shorter than the injection needle attachment portion in length along the axial direction of the nozzle portion, and
wherein the locking piece is configured to lock a proximal end portion of the cap member.

6. A pre-filled syringe comprising:
a cylindrical container including a nozzle portion provided on a distal end portion, and a cylindrical injection needle attachment portion radially spaced from and surrounding the nozzle portion to form a first space and to which an injection needle is to be attached, and a connecting tool attachment portion radially spaced from and surrounding the injection needle attachment portion to form a second space and to which one end of a connecting tool is configured to be detachably attached, and
a plunger configured to be inserted into the cylindrical container from a proximal end side of the cylindrical container; and
a cap member configured to be detachably fitted on an outer periphery of the injection needle attachment portion, the cap member having a sidewall extending into the second space and a top wall having an opening in a center of the top wall,
the injection needle attachment portion having a guiding groove in an inner periphery thereof, the guiding groove being configured to engage with an engagement protrusion provided at a proximal end of an injection needle, the guiding groove providing a guide for movement of an injection needle, wherein the opening of the cap member is larger than a diameter of the nozzle portion and smaller than an inner diameter of the injection needle attachment portion to allow a stopper member to be inserted therein, the stopper member being configured to liquid-tightly seal the nozzle portion, the opening being configured not to allow the proximal end portion of an injection needle to be inserted therein, wherein, in a state where the cap member is fitted into the second space and on the outer periphery of the injection needle attachment portion, at least a part of an edge of the opening is located on an inner side relative to a bottom portion of the guiding groove when viewed in an axial direction of the nozzle portion.

7. The pre-filled syringe according to claim 6, wherein the opening is circular in shape, wherein the guiding groove comprises a spiral groove, and wherein an inner diameter of the opening is smaller than a root diameter of the spiral groove.

8. The drug delivering apparatus according to claim 1, wherein the connecting tool attachment portion has a threaded surface.

9. The pre-filled syringe according to claim 6, wherein the connecting tool attachment portion has a threaded surface.

10. The drug delivering apparatus according to claim 1, wherein the nozzle portion, the injection needle attachment portion and the connecting tool attachment portion are integrally formed with the cylindrical container.

11. The pre-filled syringe according to claim 6, wherein the nozzle portion, the injection needle attachment portion and the connecting tool attachment portion are integrally formed with the cylindrical container.

* * * * *